United States Patent [19]

Daggett et al.

[11] Patent Number: 4,879,239

[45] Date of Patent: * Nov. 7, 1989

[54] METHOD OF CULTURING FREEZE-DRIED MICROORGANISMS AND RESULTANT PREPARATION

[75] Inventors: Pierre-Marc Daggett, Rockville; Frank P. Simione, Olney, both of Md.

[73] Assignee: American Type Culture Collection, Rockville, Md.

[*] Notice: The portion of the term of this patent subsequent to Jun. 9, 2004 has been disclaimed.

[21] Appl. No.: 905,175

[22] Filed: Sep. 9, 1986

Related U.S. Application Data

[63] Continuation-in-part of Ser. No. 548,418, Nov. 3, 1983, Pat. No. 4,672,037.

[51] Int. Cl.$^4$ .................... C12N 1/20; C12N 1/16; C12N 1/04; C12Q 1/06
[52] U.S. Cl. .................... 435/252.1; 435/39; 435/255; 435/260; 435/802; 435/810
[58] Field of Search .............. 435/253, 260, 810, 39, 435/802, 255, 252.1

[56] References Cited

U.S. PATENT DOCUMENTS

| | | | |
|---|---|---|---|
| Re. 28,488 | 7/1975 | Farr | 435/253 |
| 1,929,085 | 10/1933 | Suehs | 435/260 |
| 2,376,333 | 5/1945 | Ark | 435/260 |
| 2,738,273 | 3/1956 | Muhrer | 435/260 |
| 2,853,797 | 9/1958 | Graham et al. | 435/255 |
| 2,908,614 | 10/1959 | Muggleton et al. | 435/260 |
| 3,135,663 | 6/1964 | Muggleton et al. | 435/253 |
| 3,168,796 | 2/1965 | Scott et al. | 435/260 |
| 3,261,761 | 7/1966 | Anderson | 435/260 |
| 3,356,574 | 12/1967 | Smith | 435/253 |
| 3,360,440 | 12/1967 | Haab et al. | 435/34 |
| 3,449,209 | 6/1969 | Cameron | 435/253 |
| 3,671,400 | 6/1972 | Cekoric, Jr. et al. | 435/260 |
| 3,897,307 | 7/1975 | Porubcan et al. | 435/253 |
| 3,922,203 | 11/1975 | Aldridge, Jr. et al. | 435/34 |
| 4,140,800 | 2/1979 | Kline | 426/61 |
| 4,205,132 | 5/1980 | Sandine et al. | 435/260 |
| 4,226,940 | 10/1980 | Storrs | 435/260 |
| 4,672,037 | 6/1987 | Daggett et al. | 435/253 |

FOREIGN PATENT DOCUMENTS

53-75384 7/1978 Japan .................. 435/260

OTHER PUBLICATIONS

American Type Culture Collection Methods, "Laboratory Manual on Preservation Freezing and Freeze-Drying", 1980.

*Primary Examiner*—Elizabeth C. Weimar
*Attorney, Agent, or Firm*—Burns, Doane, Swecker & Mathis

[57] ABSTRACT

A preparation of freeze-dried microorganisms and a method for preparing a freezed-dried suspension of microorganisms and culture medium, in which the freeze-dried microorganisms can be directly cultured via addition of setrile, distilled water. The freeze-dried preparation contains a sufficient amount of a colloidal component, such as gelatin, to form the microorganisms into a microbial plug.

6 Claims, No Drawings

METHOD OF CULTURING FREEZE-DRIED MICROORGANISMS AND RESULTANT PREPARATION

This application is a continuation-in-part of application Ser. No. 548,418 filed 11/3/83, now U.S. Pat. No. 4,672,037.

BACKGROUND OF THE INVENTION

1. Field of the Invention

This invention broadly relates to a new method of culturing freeze-dried microorganisms, as well as to a new method of freeze-drying microorganisms and the product resulting therefrom. The present invention particularly pertains to a method of freeze-drying microorganisms in a vessel with nutrients so as to produce a freeze-dried preparation containing viable microorganisms that undergo substantial logarithmic or exponential growth directly in the vessel upon rehydration with sterile, distilled water. This invention has utility in diagnostic applications, such as in research and in clinical laboratories, and as an educational tool.

2. Description of the Prior Art

Freeze-drying has long been considered a simple and economical way to preserve cultures for future experimentation, reference or comparison. Freeze-drying produces a dry preparation generally capable of being stored for long periods of time while retaining biological activity. The process is broadly described in *American Type Culture Collection Methods, I. Laboratory Manual on Presentation: Freezing and Freeze-Drying*, Hatt, H. (ed.), A.T.C.C. (1980) with specific reference to processing suitable for different microorganisms. The above-referenced manual describes both the conventional procedures suitable for freeze-drying a wide variety of microorganisms and equipment suitable for carrying out the procedures.

When the moisture content of a culture is removed during the freeze-drying process, molecules are virtually locked in position so that little or no opportunity exists for alteration of the physical or chemical properties of the product. Obviously, in preparing such products it is of prime importance that the viability of the culture be maintained. In order to protect the organisms, the freeze-drying process generally is carried out in the presence of a variety of cryoprotectant agents, designed to minimize cellular damage and increase survivability of microorganisms during the freeze-drying process. Cryoprotectant agents used in the prior art have included glucose,, sucrose, lactose, mannitol, glycerol, dextran, fructose, and other materials such as monosodium glutamate polyvinylpyrrolidone (PVP), sweet whey solids, dried skim milk, dried whole milk and bovine serum albumin.

It is also common to include a small amount of fresh nutrient media (e.g., nutrient broth) in the concentrated microorganism culture prior to freeze-drying. The nutrient media is used as a biologically compatible suspending agent. The nutrient media may also function as a cryoprotectant and also provides an immediate food source for the microorganisms upon their revitalization. The prior art, however, dose not disclose a process for freeze-drying microorganisms in a vessel wherein the proportion of microorganisms to nutrient media in the suspension to be freeze-dried is adjusted so that when the freeze-dried preparation is properly rehydrated with sterile, distilled water, an active, growing culture is produced in situ.

The prior art always has used a concentration of organisms in relation to the quantity of nutrients added with the suspending liquid such that standard rehydration of the freeze-dried preparation with sterile, distilled water produces a non-dormant culture in a substantially stationary growth phase of development. Rehydration generally is accomplished by mixing the freeze-dried preparation with suitable nutrient broth, sterile distilled water, etc. Thereafter, propagation of the culture normally is accomplished by inoculating freshly prepared growth media with all or part of the rehydrated preparation. In other words, freeze-dried preparations of microorganisms always have been used to propagate numerous fresh cultures using freshly prepared, external nutrient medium rather than being used directly in the vessel in which they are stored to propagate a single culture in situ.

It is an object of the present invention to provide a simple method of establishing a growing culture in a vessel, such as in a small vial, from a freeze-dried preparation of microorganisms.

It is also an object of the present invention to provide a method of reconstituting a freeze-dried preparation of microorganisms which eliminate the need for preparing or supplying fresh nutrient medium with the freeze-dried preparation in order to develop an actively growing and multiplying culture from the freeze-dried preparatin of microorganisms.

It is another object of this invention to provide a method of freeze-drying microorganisms and nutrients in a vessel so that an active, growing culture is produced in situ merely by rehydrating the freeze-dried preparation with sterile, distilled water.

It is still another object of this invention to provide a vessel having a specific freeze-dried composition of microorganisms, nutrients and optionally a cryoprotective agent, such that simple addition of a proper amount of sterile, distilled water to the vessel produces an active, growing culture therein.

These and other objects which will become apparent from the following description are provided by the present invention.

SUMMARY OF THE INVENTION

In a first aspect, the present invention comprises a method of establishing a growing culture in a vessel comprising (a) providing a sealed vessel containing a freeze-dried preparation of microorganisms and nutrients, the number of viable microorganisms and the amount of nutrients in said freeze-dried preparation being such that the nutrients are sufficient to support substantial logarithmic growth of the viable microorganisms, and (b) unsealing said vessel and adding water thereto to initiate the logarithmic growth of said viable microorganisms.

In another aspect, the present invention comprises a sealed vessel containing a freeze-dried preparation of microorganisms and nutrients, the number of viable microorganisms and the amount of nutrients in said freeze-dried preparation being such that upon the addition of water to said vessel the nutrients are sufficient to support substantial logarithmic growth of the viable microorganisms in said vessel.

In yet another aspect, the present invention comprises a method of freeze-drying microorganisms and nutrients in a vessel to produce a freeze-dried preparation therein comprising:

a. growing a culture of the microorganisms in a nutrient medium;
b. forming a cell concentrate from said culture;
c. adding fresh nutrient medium to the cell concentrate to form a cell suspension;
d. freeze-drying the cell suspension in a vessel to produce a freeze-dried preparation in said vessel, and
e. providing an amount of nutrients in said fresh nutrient medium so that said nutrients are sufficient to support substantial logarithmic growth of the viable microorganisms in said freeze-dried preparation.

In a further aspect, the present invention provides a method of establishing a growing culture in a vessel comprising:

a. growing a culture of the microorganisms in a nutrient medium;
b. forming a cell concentrate from said culture;
c. adding fresh nutrient medium to the cell concentrate to form a cell suspension;
d. freeze-drying the cell suspension in a vessel to produce a freeze-dried preparation in said vessel;
e. providing an amount of nutrients in said fresh nutrient medium so that said nutrients are sufficient to support substantial logarithmic growth of the viable microorganisms in said freeze-dried preparation; and
f. rehydrating said freeze-dried suspension in said vessel with water so that the viable microorganisms in said freeze-dried suspension, upon proper incubation, undergo substantial logarithmic growth.

DETAILED DESCRIPTION

The present invention relates to a method of freeze-drying microorganisms and nutrients in a vessel so as to produce a freeze-dried preparation that undergoes substantial logarithmic growth directly in the vessel upon rehydration with water. In order to avoid adding any other organism or potentially toxic material to the freeze-dried preparation, the preparation preferably is rehydrated using sterile, distilled water. Accordingly, the use of sterile, distilled water will be emphasized throughout the remaining specification.

As used herein, the phrase "substantial logarithmic growth" means that the ending cell population (i.e., the cell population at the stationary phase) is at least about 10 times greater than the initial rehydrated viable cell population. Preferably, the amount of nutrients and number of viable microorganisms in the freeze-dried preparation are adjusted so that a population increase of at least 100 times occurs in the rehydrated suspension. The phrase "a concentration of viable microorganisms substantially below the concentration that would prevail during the microorganisms stationary growth phase" is a related expression which means that the initial cell population in the rehydrated suspension is at least 10 times less than the ending cell population (i.e., the cell population at the stationary phase).

The term "culture" describes a population of microorganisms cultivated or grown in a nutrient medium.

Also as used herein the phrases "fresh nutrient medium," "suitable nutrient medium" and the like mean an aqueous solution or suspension of nutrients which are necessary and sufficient to support the growth of the microorganism being freeze-dried.

Freeze-drying or lyophilization is generally recognized as an effective procedure for preserving microorganisms. In this process, microorganisms are dried while they are frozen. In Carrying out the method of this invention, the microorganisms initially are grown in any suitable nutrient medium, preferably using the best nutrient medium for the particular genus and species of microorganism to be freeze-dried. Suitable nutrient or growth medium generally contains, in addition to a carbon source, the usual and necessary nutrients, such as, for example, a nitrogen source; sources of sulfur and phosphorus; inorganic materials such as trace metals; growth factors; oxygen and carbon dioxide. The nutrient medium generally is prepared from commercially available materials suitable for the microorganism being freeze-dried, e.g., Bacto Nutrient Broth (Difco Co., Detroit, Mich.).

The composition of a suitable aqueous nutrient medium or basal medium suitable for cultivating a particular microorganism strain will readily be recognized by one skilled in the art. Moreover, it is specifically contemplated that the concentration of specific nutrients in the nutrient medium can be selected so as to influence the growth of the microorganisms in any desired manner. The medium can be prepared, for example, by dissolving or suspending the proper ingredients (nutrients) in distilled water, followed, if necessary, by sterilization and aseptic transfer into the culture. As noted above, generally a commercially available, pre-prepared nutrient source is used. The microorganisms are incubated, preferably within their optimum temperature range, often until they reach the maximum stationary phase. In the practice of this invention, incubation times vary from one microorganism strain to another, depending on the growth medium, temperature and growth characteristics of the microorganism. For example, vegetative material generally is harvested in the mid- to late-logarithmic phase of growth.

The method of this invention is applicable to a wide variety of microorganisms, including algae, fungi (including yeast), bacteria and protozoa. As noted above, suitable nutrient media and growth conditions applicable to particular microorganism strains are evident to one skilled in this art. For example, bacteria generally are capable of growing over a wide range of physical conditions and are capable of utilizing many different nutrients, but as is well-known, optimal growth requires certain specific conditions for a given species. Suitable commercially available nutrient media for several organisms are identified in the examples included hereafter.

After harvesting the incubated culture, a cell concentrate is prepared from the culture of microorganisms. The concentrate can be obtained, for example, by centrifuging the previously grown culture, and removing the aqueous supernatant. This step removes any metabolic by-products which may interfere with the microorganism's survival during the freeze-drying process and/or materials which may inhibit growth after subsequent rehydration. Other methods of preparing a cell concentrate will be apparent to one skilled in the art. Afterwards, the cell concentrate is suspended in fresh, sterile nutrient medium.

The cell concentrate is diluted with a predetermined volume of a known concentrate of fresh nutrient medium to produce a cell suspension Generally, the nutrient medium employed for preparing the cell suspension has the same nutrient components as the medium initially used to grow the culture, but the nutrients are present at a higher concentration. Previous comments concerning the nutrient medium content used to grow the microorganism are equally applicable with respect to the fresh nutrient medium used to form the cell suspension.

The present invention has as an objective the formation of a freeze-dried preparation of microorganisms and nutrient medium in a vessel, such that simple addition of a proper amount of sterile, distilled water thereto produces an actively growing culture in situ. In order to determine the volume and concentration of nutrient medium needed in any given case it initially is necessary to fix (ascertain) the concentration of cells in the cell concentrate and determine what proportion or number of those cells will survive the freeze-drying process, i.e., the proportion of viable microorganisms in the freeze-dried preparation. These values can readily be determined by routine experimentation, e.g., by using direct or indirect cell counting techniques, and generally remain quite constant for a given strain of microorganism which is cultivated, harvested (i.e., preparation of cell concentrate) and freeze-dried using closely reproduced procedures. A volume and concentration of the fresh nutrient medium then is selected so that the resulting freeze-dried preparation produced from the cell suspension contains a number of viable microorganisms, i.e., a number of microorganisms which survive the freeze-drying process, in mixture with an amount (content) of nutrients such that when the freeze-dried preparation is rehydrated with a suitable volume of sterile, distilled water the rehydrated suspension contains a concentration of viable microorganisms substantially below the concentration that would prevail during the microorganisms stationary growth phase in admixture with a concentration of nutrients sufficient to support substantial logarithmic growth of the microorganisms.

The rehydrated culture must contain a suitable concentration of nutrients to support substantial logarithmic growth of the micro-organisms after the freeze-dried preparation has been rehydrated with sterile water. Generally, the rehydrated suspension will contain a concentration of viable microorganisms less than or about $10^7$ cells per ml. The general relationship between the cell concentrate, the volume and concentration of the fresh nutrient medium used to prepare the cell suspension, and the suitable volume of sterile, distilled water used to rehydrate the freeze-dried preparation is represented in the following equations and best illustrated by the following hypothetical example. Examples of specific microorganisms are presented in detail hereafter.

$$V_{fn}[k\, f_1 C_c V_c]/[C_{sd} f_2] \quad (1) \text{ and}$$

$$V_{H_2O} = [k f_1 C_c V_c]/C_{sp} \quad (2)$$

$$f_2 = [V_{H_2O}/V_{fn}] = [C_{fn}/C_{rs}] \quad (3)$$

where
- $V_{fn}$ = the predetermined volume of fresh nutrient medium
- $V_{H_2O}$ = a suitable volume of sterile, distilled water used for rehydrating the freeze-dried suspension
- $f_1$ = the fraction of cells in the cell concentrate which will survive the freeze-drying process, i.e., the fraction of viable cells in the freeze-dried preparation
- $C_c$ = the concentration of microorganisms in the cell concentrate
- $V_c$ = the volume of the cell concentrate
- $C_{sp}$ = the stationary phase concentration of microorganisms in the rehydrated suspension
- $f_2$ = the ratio of the concentration of nutrients in the fresh nutrient medium ($C_{fn}$) to the concentration of nutrients desired in rehydrated suspension ($C_{rs}$)
- k = a constant, equal to or greater than 10, which represents the magnitude of growth desired in the rehydrated suspension Micoorganism strain A when incubated in its optimum nutrient medium reaches a stationary phase population of about $10^7$ cells per ml. A cell concentrate prepared from this culture by a standard centrifugation program has a volume of 0.1 ml ($V_c$) and contains about $5 \times 10^7$ cells per ml ($C_c$). When this concentrate is freeze-dried using a standard freeze-drying procedure, about 80% of the cells will survive a given period of storage under appropriate conditions ($f_1 = 0.8$). As a result, under these particular conditions the cell concentrate contains about $4 \times 10^7$ viable cells per ml, i.e. cells which will survive the freeze-drying process.

In order for this microorganism to undergo a substantial logarithmic growth when rehydrated it is necessary that the rehydrated suspension contain less than $10^6$ cells per ml, (i.e., an increase in organism population of at least 10 times; k=10), provided that the incubation conditions for the rehydrated suspension (including the concentrate of nutrient mddium) closely parallel the conditions initially used to grow the culture (recall that the assumed stationary phase population is about $10^7$ cells per ml). In-other words, in this case $C_{sp} = 10^7$. To obtain a rehydrated suspension containing less than $10^6$ cells per ml, the freeze-dried suspension must be diluted with about 4 ml of sterile, distilled water (Equation (2)), thereby fixing a suitable volume of rehydration water for the freeze-dried preparation. Obviously a little more or less rehydration water is possible and to some extent will effect population dynamics. However if too much rehydration water is used then the concenration of nutrients will be too low to support growth. On the other hand, if too little rehydration water is added then the resulting concentration of nutrients will be toxic to the microorganisms. Based on this disclosure one skilled in this art will readily recognize the permissible range in the amount of rehydration water added to initiate substantial logarithmic growth of the microorganisms.

Prefereably, the concentration of nutrients in the fresh nutrient medium added to the, cell concentrate is greater than would normally be used to grow the organism in the rehydrated suspension so as to minimize the quantity of water that must be removed during the freeze-drying process, i.e., $f_2 \geqq 1$. For example, nutrients at a level of at least two times the standard is preferred ($f_2 = 2$). The quantity (volume) of fresh nutrient medium required can then be calculated from Equation (1).

As discussed above, the fresh nurient medium preferably is prepared such that the optimum composition for the particular genus and species being freeze-dried is produced upon rehydration. In this hypothetical example, with $f_2 = 2$, the cell concentrate would be diluted with about 2 ml of double strength fresh nutrient medium to produce the cell suspension.

It should be noted, the preceding equations need not be applied rigidly; values calculated therefrom are preferably used only as guidelines. These equations are included herein primarily to illustrate and explain the present invention more completely. For convenience, a nephelometer or spectrophotometer can be used to ensure preparation of a cell suspension with a proper (approximate) cell concentration.

In the conventional freeze-drying procedure for preserving microorganisms, much higher concentrations of microorganisms are used in the cell concentrate relative to the quantity of nutrients added with any suspending liquid, so that after considering the number of cells which survive the freeze-drying process, a conventionally rehydrated suspension contains a concentration of microorganisms at or near the stationary phase.

Normally, the cell suspension of the present invention will also contain a protective menstrum or cryoprotectant. The cryoprotectant increases the survivability of the micro-organisms through the freeze-drying process. In the broad practice of this invention, any of the wide variety of cryoprotectants disclosed in the prior art can suitably be employed, and one skilled in this technology will readily recognize that certain cryoprotectants are more effective with particular strains of microorganisms. Certain of the cryo-protectants, such as dried skim milk, may produce a clouded culture upon rehydration. Such cryoprotectants are not preferred when it is desired to monitor the growth of the rehydrated suspensions using optical techniques such as spectrophotometry, nephelometry, or turbidimetry. In such instances, a cryoprotectant such as sucrose, or bovine serum albumin which adds little to the optical character of the rehydrated culture, is generally preferred.

After preparing the cell suspension, generally also containing a cryoprotectant, the suspension is freeze-dried in a suitable vessel. Preferably, the cell suspension is freeze-dried as soon as possible after its preparation. Generally, a wide variety of glass and in some cases plastic ampules and vials typically are used. Transparent vessels are particularly preferred as these permit visual inspection and optical analysis of the growing, rehydrated suspension. The vessel typically has a volume below about one liter, and vessels with a volume below 100 ml generally are used. The vessel is cleaned, sterilized and properly labelled before being used.

A complete discussion of procedures used to freeze-dry the cell suspension is beyond the scope of the present invention and procedures readily available to the prior art have been found suitable. One procedure is described in detail in the examples that follow. Generally, the above-prepared suspension will be freeze-dried by initially freezing the culture at about $-40°$ C. for about one hour (e.g., in a commercial freeze-drier) followed by evacuating the sample to low absolute pressure. During evacuation, which occurs over an extended time period, the temperature of the preparation is allowed to rise slowly to ambient conditions. Any standard freeze-drying equipment can suitably be used in the practice of the present invention. For a detailed description of proper procedures and equipment suitable for freeze-drying microorganisms in the broad practice of the present invention, please refer to the ATCC Laboratory Manual on Preservation: Freezing and Freeze-Drying referenced earlier, the disclosure of which is incorporated in its entirety herein.

After the last desired amount of moisture has been removed, the vessel containing the freeze-dried preparation of microorganism and nutrients is properly sealed and is now ready for storage. The vessel contains a quantity of freeze-dried microorganisms and freeze-dried nutrients such that upon proper rehydration and incubation an active microbial culture is produced in situ which culture undergoes substantial logarithmic growth from an initial cell population to an ending cell population.

The vessel containing the freeze-dried preparation can be stored under ambient conditions, although storage at a constant temperature below about $5°$ C. will prolong the length of survival of the freeze-dried microorganisms. One skilled in this art will recognize whether a particular microorganism strain requires additional special storage conditions, otherwise standard storage practices are proper.

In accordance with the method of this invention, a growing culture of the freeze-dried microorganisms can now be re-established simply by rehydrating the freeze-dried preparation with a suitable volume of sterile distilled water directly in the storage vessel. The seal of the vessel is broken and a quantity of water necessary to adjust the concentration of nutrients in the rehydrated suspension to a concentration suitable for supporting substantial logarithmic growth of the viable microorganisms in the freeze-dried suspension is added to the vessel. In this way, the proper concentration of nutrient medium is established in situ. The vessel containing the rehydrated suspension is then incubated under conditions, e.g., light, oxygen, temperature, etc., appropriate for the species of microorganism involved. After a short lag, the cell population enters the exponential or logarithmic phase of rapid growth. During this phase of growth, the cells divide steadily at a substantially constant rate. The cell population undergoes substantial logarithmic growth from an initial cell population to an ending cell population, corresponding to the constant cell population existing at the stationary phase of growth. The trend toward cessation of growth is generally caused by the depletion of some nutrients. In some cases it may be caused by the production of toxic by-products of growth. Generally, after reaching the stationary phase the cell population will remain constant for a certain period of time.

By freeze-drying the microorganisms culture (cell suspension) in a transparent vessel, and by employing a cryoprotectant that does not adversely affect the optical characteristics of the rehydrated suspension, the progress of the cell population can readily be monitored by optical techniques such as spectrophotometry, nephelometry, and turbidimetry. In this way, the product of this invention is useful, for example, as an educational tool for teaching students about cell population dynamics, reproduction and growth. As an educational aid, the product of this invention is supplied as a kit. The kit comprises a package which includes one transparent vessel containing the freeze-dried preparation of microorganisms and nutrients and a second vessel containing a suitable amount of sterile, distilled water for rehydrating the freeze-dried preparation. The product of this invention also has application in research and in chemical laboratories, for example, in diagnostic applications, or in any application where an actively growing culture generally is prepared from a freeze-dried preparation.

As a check on diagnostic procedures, clinical laboratories generally require a known culture of the specific bacteria being examined or detected in order to verify the accuracy of their procedures and the suitability of their reagents. Consequently, there is a demand for a readily available and economic source of viable, standard-reactive microorganisms. The present invention not only adequately satisfies this need but does so in a simple, convenient and economical manner.

The present invention eliminates the need for preparing or supplying fresh sterile nutrient medium each time an actively growing culture is prepared from a freeze-dried preparation of microorganisms. Consequently, both the time and expense of preparing an active culture from a freeze-dried sample is substantially reduced.

The following examples are included for illustrative purposes only and are not itended to limit the scope of this invention.

EXAMPLE 1

A pure culture of *Bacillus subtilis* a specific strain available from the American Type Culture Collection number 6051 was grown as a test tube culture in Bacto Nutrient Broth DIFCO 0711. When the cell population reached late log, the cells were harvested and a cell concentrate was prepared by centrifuging the culture. The cells then were resuspended in double strength Bacto Nutrient Broth DIFCO 0711 containing 12% (v/v) sucrose and 5% (v/v) bovine serum albumin to obtain a cell suspension of about $10^7$ cells per ml. The cell concentration was verified using a spectrophotometer.

Thereafter, 1.0 ml of the cell suspension was added to a 4.0 ml transparent glass vial. The vessel was plugged with a butyl rubber stopper and the culture was freeze-dried by placing the vial on the precooled ($-40°$ C.) shelf of a Virtis 25 SRC-MS sublimator and allowing the product to cool to $-40°$ C. (product temperature monitored). The sublimator chamber was evacuated to less than 50 microns (Hg), condenser at $-55°$ C.; shelf warmed to $-30°$ C. and sublimation allowed to proceed for about 68 hours. Shelf temperature was then raised to 30° C. and drying continued until product temperature reached 20° C. Vials were back filled with sterile $N_2$ and stoppered. Part of the freeze-dried samples were then stored at about 37° C. for 80 days as part of an accelerated storage test. Storage for 80 days at 37° C. is equivalent to storage at 25° C. for 1200–1600 days.

Thereafter, the freeze-dried preparation was removed from storage, the seal on the vessel was broken and 3 ml of sterile water was added to the vessel to rehydrate the freeze-dried preparation. Upon proper incubation, the rehydrated culture exhibited substantial logarithmic growth from an initial cell population of $2.4 \times 10^4$ cells/ml.

EXAMPLE 2

A pure culture of *Escherichia coli*, a specific strain available from the American Type Culture Collection number 11775 was grown as a test tube culture in Nutrient Broth DIFCO 0711. When the cell population reached late log, the cells were harvested by centrifuging the culture and then resuspending the cells in double strength Bacto Nutrient Broth DIFCO 0711 containing 12% (v/v) sucrose and 5% (v/v) bovine serum albumin to obtain a cell concentration of about $10^7$ cells/ml. The cell concentration was verified using a spectrophotometer.

Thereafter, 1.0 ml of the cell concentrate was added to a 4.0 ml transparent glass vial. The vessel was plugged with a butyl rubber stopper and the culture was freeze-dried using the same procedure as Example 1.

After the same accelerated storage period as in Example 1 the freeze-dried preparation was removed from storage, the seal on the vessel was broken and 3.0 ml of sterile water was added to the vessel to rehydrate the culture. Upon proper incubation, the rehydrated culture exhibited substantial logarithmic growth from an initial cell population of $2.9 \times 10^5$ cells/ml.

EXAMPLE 3

A pure culture of *Serratia marcesens*, a specific strain available from the American Type Culture Collection number 8195 was grown as a test tube culture in Bacto Nutrient Broth DIFCO 0711. When the cell population reached late log, the cells were harvested by centrifuging the culture and then resuspending the cells in double strength Bacto Nutrient Broth DIFCO 0711 containing 12% (v/v) sucrose and 5% (v/v) bovine serum albumin to obtain a cell concentrate of about $10^7$ cells/ml. The cell concentration was verified using a spectrophotometer.

Thereafter, 1.0 ml of the cell concentrate was added to a 4 0 ml transparent glass vial. The vessel was plugged with a butyl rubber stopper and the culture was then freeze-dried using the same procedure as Example 1.

After the same accelerated storage period as in Example 1, the freeze-dried preparation was removed from storage, the seal on the vessel was broken and 3.0 ml of sterile water was added to the vessel to rehydrate the culture. Upon proper incubation, the rehydrated culture exhibited substantial logarithmic growth from an initial cell population of $6.3 \times 10^3$ cells/ml.

EXAMPLE 4

A pure culture of *Rhodototorula rubra*, a specific strain available from the American Type Culture Collection number 9449 was grown as a test tube culture in Bacto YM Broth DIFCO 0003-01-6. When the cell population reached late log, the cells were harvested by centrifuging the culture and then resuspending the cells in double strength Bacto YM Broth DIFCO 0003-01-6 containing 12% (v/v) sucrose and 5% (v/v) bovine serum albumin to obtain a cell concentrate of $1.7 \times 10^7$ cells/ml.

Thereafter, 1.0 ml of the cell concentrate was added to a 4.0 ml transparent glass vial. The vessel was plugged with a butyl rubber stopper and the culture was freeze-dried using the same procedure as Example 1.

After freeze-drying, the seal on the vessel was broken and 3.0 ml of sterile water was added to the vessel to rehydrate the culture. Upon proper incubation, the rehydrated culture exhibited substantial logarithmic growth from an initial cell population of $9 \times 10^6$ cells/ml.

The foregoing description of the present invention has focused primarily on an embodiment wherein the freeze-dried preparation of microorganisms is rehydrated in the same vessel in which the preparation of microorganisms was freeze-dried. In an alternative embodiment described below, the freeze-dried preparation, containing at least concentrated medium and microorganisms, is configured in a shape, e.g. a plug which is removed from the container in which it is freeze-dried, stored in another vessel and subsequently rehydrated. Rehydration is typically accomplished by placing the plug in an amount or volume of water sufficient to bring the concentration of the medium to $1 \times$. Accordingly, when the present invention is embodied in a plug, rehydration does not take place in situ since the freeze-dried preparation is removed from the vessel in which it is freeze-dried and is rehydrated by placing the plug in a separate container with a volume of water sufficient to bring the concentration of the medium to 1× which enables substantial logarithmic growth of the viable microorganisms.

Providing freeze-dried preparations of microorganisms in plugs is known in the art. The propagation of a culture using the prior art normally is accomplished by inoculating freshly prepared growth media with all or a part of the rehydrated preparation. In other words, freeze-dried preparations of microorganisms configured as plugs have been used to propagate fresh cultures using freshly prepared external nutrient medium. In the present invention, the freeze-dried preparation in plug form is produced so that no external nutrient medium is required and when the plug is combined with an appropriate amount of water substantial logarithmic growth of the viable microorganisms will occur.

As explained above in the context of in situ rehydration, in the present invention, there is a relationship between the volume of the plug, the microorganism concentration before freeze-drying, the volume of the culture desired upon rehydration and the concentration of the medium in the plug. For instance, if a 0.1 ml plug is formed, a 50× concentration of medium would be needed to provide a rehydrated culture of 5.0 ml medium of normal concentration. A 25× concentration of medium is needed to provide a rehydrated 5.0 ml culture if the plug has a volume of 0.2 ml. If a 10.0 ml culture is desired from a 0.2 ml plug then 50× concentration of medium would be required. The relationship between the plug, microorganism concentration, medium concentration and volume of the culture desired upon rehydration is illustrated in Example 5.

Applicants have found that it is sometimes desirable to add a colloidal compound to the cell suspension prior to freeze drying. The addition of such colloidal compound provides a freeze dried preparation with enhanced mechanical characteristics suitable for formation of a plug which retains its shape after freeze-drying when the plug is removed from the container, e.g., the wells in which it was freeze-dried. The physical characteristics of some media, however, provide a plug without addition of colloidal compounds. When addition of a colloidal compound is desirable, however, the preferred colloidal compound for use with most freeze-dried preparations is gelatin. The amount of colloidal compound used should be selected to provide a plug which dissolves when the plug is placed in water. For gelatin-containing plugs, applicants have found the use of from about 0.5% to 1.5% gelatin (w/v) of the cell suspension prior to freeze-drying is preferred and use of about 1.0% is most preferred. The techniques for using colloidal compounds such as gelatin to form a plug of freeze-dried microorganisms are known to those of ordinary skill in the art of freeze-drying microorganisms.

The following procedures may be followed to provide a freeze-dried preparation in a plug configuration. To provide a cell suspension for freeze-drying, a growth medium for the microorganism is provided in concentrated form. The concentration of the medium is based upon the plug volume and the final volume of single strength medium desired upon rehydration. For example, if the plug volume is 0.2 ml then 25× concentration of medium is used for a 5.0 ml culture. The concentration of the microorganism and the medium in the cell suspension is selected to ensure that after freeze-drying substantial logarithmic growth will occur upon rehydration with an amount of water sufficient to establish logarithmic growth. The cell suspension is dispensed into the small wells of a microtiter plate or other suitable device for forming a plug during the freeze-drying process. Microtiter wells used in a laboratory commonly hold 0.1 to 0.3 ml. The cell suspension is then freeze-dried in a conventional manner. After freeze drying the plugs are popped out of the microtiter plate aseptically and placed in vials or other suitable containers for storage. Several plugs may be contained within one vial.

To rehydrate a plug of the present invention, the plug is aseptically removed from its storage container and combined with a volume of sterile distilled water such that the resulting medium will be at single strength. Upon rehydration in an amount of water sufficient to provide a medium at single strength, substantial logarithmic growth of the viable microorganisms in the plug of freeze-dried microorganism will occur.

The plug configuration of applicants' invention is illustrated by Example 5 below. It must be understood, however, that the size of plug and the end volume of rehydrated material may be either smaller or much larger than the size and volumes used in Example 5 to illustrate the invention. The upper limit on the size of plug is presently determined primarily by the practical and economic considerations associated with freeze-drying large volumes of material and the extent to which medium can be concentrated.

EXAMPLE 5

The following test of the plug configuration was conducted with the bacterial strain *Escherichia coli* ATCC® 11775. Microtiter plates which had wells which would hold at least 0.2 ml were used. A final culture volume of 5.0 ml was desired, thus a 25× concentration of nutrient broth medium was used in the preparation. In this example, w designates the weight of the ingredient and v designates the volume of water present prior to freeze-drying. The menstrum also contained 12% (w/v) sucrose, 5% (w/v) bovine serum albumin fraction five and gelatin. Two concentrations of gelatin were tested 0.5% (w/v) and 1.0% (w/v). The initial microorganism concentration of $3.0 \times 10^9$ cells/ml for the 0.5% gelatin preparation and $1.5 \times 10^{10}$ cells of the 1.0% gelatin preparation respectively. Upon rehydration for the 0.5% gelatin preparation there were approximately $4 \times 10^7$ viable cells per ml. For the 1.0% gelatin preparation, there were approximately $2.0 \times 10^8$ viable cells per ml. After freeze-drying, plugs were removed from the microtiter wells. The plugs were then rehydrated by placing them in a container holding 5.0 ml sterile distilled water. After rehydration and 48 hours of growth the microorganism concentration was $1.0 \times 10^{12}$ cells/ml for the 0.5% gelatin preparation and $1.0 \times 10^{11}$ cells/ml for the 1.0% gelatin preparation respectively.

While specific embodiments of this invention have been described herein, those skilled in the art will appreciate that changes and modifications may be made without departing from the spirit and scope of this invention, as defined in and limited only by the scope of the appended claims.

We claim:

1. A freeze-dried preparation of microorganisms comprising a population of viable microorganisms which survive freeze-drying and nutrient medium in a sealed vessel, said nutrient medium added prior to freeze-drying, wherein the population of viable microorganisms which survive freeze-drying is determined prior to freeze-drying to ensure that the population of viable microorganisms which survive freeze-drying relative to the concentration and volume of nutrients in said nutrient medium is sufficient to support substantial logarithmic growth of the population of viable microorganisms in said preparation upon rehydration with a fixed volume of water, wherein said fixed volume of water is sufficient to initiate substantial logarithmic growth of said population of viable microorganisms in said preparation and a sufficient amount of colloidal component to form said freeze-dried preparation of microorganisms into a plug.

2. A freeze-dried preparation as recited in claim 1 wherein said colloidal compound is gelatin.

3. A freeze-dried preparation as recited in claim 2 wherein said gelatin is present in said freeze-dried preparation in an amount from about 0.5% to 1.5% (w/v) of a cell suspension used to form said freeze-dried preaparation.

4. A method of preparing a freeze-dried preparation of microorganisms comprising the steps of:
   a. growing a culture of the microorganisms in a nutrient medium;
   b. forming a cell concentrate from said culture;
   c. determining the population of microorganisms which must survive freeze drying to provide a population of viable microoganisms after freeze-drying which will enter substantial logarithmic growth upon rehydration with a fixed volume of water, wherein said fixed volume of water is detemrined to be sufficient to initiate substantial logarithmic growth of said polulation of viable microorganisms;
   d. forming a cell suspension of microorganisms for freeze-drying by adding fresh concentrated nutrient medium to said cell concentrsate whereby the concentration and volume of nutrients in said nutrient medium relative to the number of said microorganisms in said cell suspension provides a cell population of viable microorganism after freeze-drying which will enter substantial logarithmic growth when said preparation is rehydrated in said vessel with said field volume of water;
   e. adding a suffcient amount of colloidal compound to said cell suspension to form a plug; and
   f. freeze-drying said cell suspension in a vessel to produce a freeze-dried preparation in said vessel.

5. A method as recited in claim 4 wherein said collodial compound is gelatin.

6. A method as recited in claim wherein said gelatin is present in said cell suspension in an amount from about 0.5% to 1.5% by weight of said cell suspension.

* * * * *

UNITED STATES PATENT AND TRADEMARK OFFICE
CERTIFICATE OF CORRECTION

PATENT NO. : 4,879,239

DATED : November 7, 1989

INVENTOR(S) : Pierre-Marc DAGGETT and Frank P. SIMIONE

It is certified that error appears in the above-identified patent and that said Letters Patent is hereby corrected as shown below:

Claim 6, line 1, after "claim" insert - - 5 - -.

Signed and Sealed this

Twenty-third Day of October, 1990

*Attest:*

HARRY F. MANBECK, JR.

*Attesting Officer*  *Commissioner of Patents and Trademarks*